United States Patent
Weerasooriya et al.

(10) Patent No.: US 7,119,236 B2
(45) Date of Patent: Oct. 10, 2006

(54) METHOD OF PREPARING ALKOXYLATION CATALYSTS AND THEIR USE IN ALKOXYLATION PROCESSES

(75) Inventors: Upali Peter Weerasooriya, Austin, TX (US); James Lyle Bennett, Topeka, KS (US); Peter Paul Radford, Lenexa, KS (US)

(73) Assignee: Harcros Chemicals Inc., Kansas City, KS (US)

( * ) Notice: Subject to any disclaimer, the term of this patent is extended or adjusted under 35 U.S.C. 154(b) by 149 days.

(21) Appl. No.: 10/832,613

(22) Filed: Apr. 27, 2004

(65) Prior Publication Data

US 2005/0240064 A1    Oct. 27, 2005

(51) Int. Cl.
*C07C 41/01* (2006.01)

(52) U.S. Cl. .................. 568/606; 568/608; 568/618; 568/620; 502/170; 502/172; 502/173; 502/340

(58) Field of Classification Search ............... 568/606, 568/608, 618, 620; 502/170, 172, 173, 340
See application file for complete search history.

(56) References Cited

U.S. PATENT DOCUMENTS

| | | | |
|---|---|---|---|
| 4,239,917 A | 12/1980 | Yang | |
| 4,754,075 A | 6/1988 | Knopf et al. | |
| 4,775,653 A | 10/1988 | Leach et al. | |
| 4,820,673 A | 4/1989 | Knopf et al. | |
| 4,835,321 A | 5/1989 | Leach et al. | |
| 4,886,917 A | 12/1989 | Knopf et al. | |
| 5,114,900 A | 5/1992 | King | |
| 5,120,697 A | 6/1992 | King | |
| 5,220,046 A | 6/1993 | Leach et al. | |
| 5,386,045 A | 1/1995 | Weerasooriya et al. | |
| 5,627,121 A | 5/1997 | Lin et al. | |
| 6,147,246 A | 11/2000 | Weerasooriya et al. | |

OTHER PUBLICATIONS

MSDS for Alfonic 1412-40, Aug. 1989, 4 pages.*
Weerasooriya, Ester Alkoxylation Technology, *Journal of Surfactants & Detergents*, vol. 2 No. 3, pp. 373-381 (1999).

* cited by examiner

Primary Examiner—Rosalynd Keys
(74) Attorney, Agent, or Firm—Stinson Morrison Hecker LLP

(57) ABSTRACT

A process for preparing an alkoxylation catalyst suitable for alkoxylating compounds that includes mixing a calcium-containing compound in a dispersing medium having a boiling point less that 160° C. with a carboxylic acid and an inorganic acid or anhydride.

53 Claims, No Drawings

METHOD OF PREPARING ALKOXYLATION CATALYSTS AND THEIR USE IN ALKOXYLATION PROCESSES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to the preparation of an alkoxylation catalyst and to a process of alkoxylation using the catalyst.

2. Description of Related Art

Alkylene oxide adducts of compounds containing "active" or "labile" hydrogens find utility in a variety of products such as, for example, surfactants, solvents, and chemical intermediates. Typically, these alkylene oxide adducts are prepared by an alkoxylation reaction in which an alkylene oxide, such as ethylene oxide, is reacted under suitable conditions with an organic compound, such as an alcohol, having one or more active hydrogen atoms. In particular, ethylene oxide adducts of aliphatic alcohols or substituted phenols having from about 8 to 20 carbon atoms have found widespread utility as non-ionic detergent components or as intermediates for anionic detergent components of cleaning formulations for use in industrial and household applications.

Among the catalysts, potassium hydroxide (KOH) is the most widely used ethoxylation catalyst in the world. This is followed by sodium hydroxide (NaOH) and to an even lesser extent by sodium methylate (NaOMe). The ethoxylates produced using these catalysts are termed broad range ethoxylates ("BREs") because they produce a broad range of alkoxylate species. See generally King, U.S. Pat. No. 5,114,900 and King, U.S. Pat. No. 5,120,697, which are incorporated by reference. These catalysts are generally used in the dry form or in an aqueous (except for NaOMe) or a methanolic medium. Prior to ethoxylation, in the case of dry catalyst, the water of reaction is removed by applying heat and vacuum or nitrogen sparge. Likewise, in the case of an aqueous or methanolic catalyst, the water or methanol is removed to generate the active catalyst prior to the start of ethoxylation of the substrate. Failure to do so results in ethoxylated by-products arising from side reactions with KOH, water or methanol.

In many instances, it is desirable to tailor the adduct number or ethoxymer distribution of a given product mixture to its intended service. For example, it is known that in surfactant applications, an adduct with too few ethylene oxide molecules is not effective because of poor water solubility. An adduct with too many ethylene oxide molecules is undesirable because surface tension reduction per unit mass decreases drastically with increasing hydrophilicity.

In order to meet this need, the prior art also contains catalysts to produce certain narrow range ethoxylates ("NRE"). For example, as taught in U.S. Pat. No. 4,239,917, which is incorporated by reference, it is desirable, particularly for surfactant applications, to use ethoxylates or alkoxylates with a narrow distribution in the desired mole adduct range of from about 2 to about 10 alkylene oxide adducts per alcohol molecule. The lower mole ethoxylates could serve as intermediates for anionic surfactants. Several references disclose the use of calcium-based catalysts for carrying out such alkoxylation reactions. See U.S. Pat. Nos. 4,754,075; 4,820,673; 4,835,321; 4,886,917; 5,220,046; 5,386,045; 5,627,121; and 6,147,246, all of which are incorporated by reference. As discussed in Lin, U.S. Pat. No. 5,627,121, these catalysts are often prepared in an alkoxylated alcohol mixture composed of alkoxylated alcohols and residual free alcohol. King, U.S. Pat. No. 5,114,900 discloses diols, such as ethylene glycol, propylene glycol, diethylene glycol, glycerol, butanediols, 1,3-propanediol, and the like as suitable dispersing media. However, the dispersing medium in these catalysts cannot be volatilized without losing a significant part of the substrate to be ethoxylated prior to ethoxylation. Consequently, the dispersing medium in the catalyst will end up being ethoxylated along with the substrate. This problem becomes even more pronounced in the case of producing higher mole ethoxylates where a higher level of the catalyst, relative to the substrate, is to be employed. This in turn will lead to correspondingly higher levels of by-products.

In sum, the prior art has taught the use of alcohol ethoxylates (Leach '321 Patent and Lin '121 Patent) or of diols or polyols (King '900 Patent) in the making of alkoxylation catalysts of high activity because of the high dispersing ability exerted by these solvents towards the calcium species. It is our surprising discovery that the use of simple short-chain alcohols and other dispersing media are effective in the production of highly active alkoxylation catalysts.

BRIEF SUMMARY OF THE INVENTION

An object of the present invention is to provide an improved NRE catalyst technology.

It is therefore an object of the present invention to provide an improved process for alkoxylating the reactants selected from the class consisting of compounds having active or labile (as in amines) hydrogen atoms, esters, and mixtures thereof.

It is a further object of the present invention to provide a process for producing a catalyst useful in the production of alkoxylated compounds having a peaked distribution of the alkoxylated species (NREs).

It is still another object of the present invention to prepare alkoxylation catalysts that can be used to ethoxylate substrates with minimal formation of by-products.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

A. Preparation of Catalyst

In preparing the alkoxylation catalyst according to the process of the present invention, a calcium-containing compound that is at least partially dispersible in a volatile organic dispersing medium is admixed together with a carboxylic acid. The calcium/carboxylic acid mole ratio ranges from about 15:1 to about 1:1. Following solubilization, an inorganic acid or anhydride is introduced into the reaction mixture. Preferably, the inorganic acid is in an amount sufficient to neutralize at least 25% of the titratable alkalinity present in the mixture. The partially neutralized composition is then optionally heated at a temperature of from about 25° C. to about 160° C. under reflux conditions for about a period of 1 to 5 hours. If it is desirable to have the catalyst in solid form, the volatile dispersing medium is then removed to generate an active catalyst prior to the subseciuent ethoxylation process.

The calcium-containing compounds used in the present invention are ones that are at least partially dispersible or soluble in the volatile dispersing medium. Examples of specific calcium-containing compounds/compositions include one or more reaction products of calcium with various alcohols (alcoholates such as calcium alkoxides and phenoxides) as well as oxide, hydroxide, carbide, and carboxylate compounds, e.g., acetates, formates, oxalates, citrates, lactates, benzoates, laurates and stearates. While compounds such as calcium hydride, calcium acetate, and calcium oxalate, may be used, it is preferred that the calcium-containing compound be calcium oxide, calcium hydroxide, or a mixture thereof.

The carboxylic acids useful in the present invention include any suitable compound having a —COOH moiety or precursors to —COOH moieties as in anhydrides. The carboxylic acids include aliphatic or aromatic compounds having a mono-, di-, or poly- —COOH moiety. While it is preferred that the carboxylic acids be saturated, they may optionally contain other functional groups such as hydroxyl groups that do not interfere with the reaction. Most preferably, the carboxylic acids of the present invention are branched chain or linear monocarboxylic acids. In addition, the preferred carboxylic acids have from about 2 to 18 carbon atoms, most preferably between 4 to about 15 carbon atoms. Most preferred carboxylic acids are those that have good miscibility in organic solvents. Non-limiting examples of such suitable acids include octanoic acid, 2-methyl hexanoic acid, heptanoic acid, 3-methyl octanoic acid, 4-ethyl nonanoic acid, and 2-ethyl hexanoic acid, or mixtures thereof.

The inorganic acids and anhydrides that are useful in the process of the present invention include sulfuric acid, phosphoric acid, polyphosphoric acid, oleum, sulfur trioxide, and phosphorous pentoxide, or mixtures thereof. Particularly preferred are the oxy acids such as sulfuric acid.

The volatile dispersing medium of the present invention "consists essentially of" media having a boiling point less than about 160° C., even more preferably less than about 150° C., still more preferably less than about 140° C., and even more preferably less than about 120 C°. The dispersing media preferably consists essentially of media having a boiling point between about 80° C. and about 160° C., and even more preferably between about 80° C. and about 120° C. As used herein, the phrase "consisting essentially of" with respect to the volatile dispersing media of the present invention means that other components may be added to the media without materially affecting the basic and novel characteristic of the invention. That is, the volatile dispersing medium of the present invention may contain minor components having higher boiling points (above 160° C.). However, these minor components preferably comprise less than 10% by weight, even more preferably less than 5% by weight, still more preferably less than 1% by weight, and most preferably less than 0.1% by weight of the total weight of the dispersing medium. Thus, as an example, the alkoxylated alcohol mixture used as the dispersing medium in Lin, U.S. Pat. No. 5,627,121, is outside the scope of the present invention.

Most preferably, the dispersing medium of the present invention "consists of" media having a boiling point less than 160° C., even more preferably less than about 150° C., still more preferably less than about 140° C., and even more preferably less than about 120° C. Most preferably, the dispersing media preferably consists essentially of media having a boiling point between about 80° C. and about 160° C., and even more preferably between about 80° C. and about 120° C. As used herein, the phrase "consisting of" excludes any ingredient that does not have a boiling point as specified.

Suitable volatile dispersing media include alcohols, esters, ethers, ketones, aldehydes, and other aliphatic and aromatic hydrocarbons having a boiling point less than 160° C., and mixtures thereof.

The preferred dispersing medium is preferably a lower straight chain or branched alcohol. Most preferably, the dispersing medium is butanol. Other suitable alcohols include, but are not limited to, methanol (65° C.), ethanol (78° C.), 1-propanol (106° C.), 2-propanol (82.5° C.), 2-methyl-2-propanol (82.4° C.), 1-butanol (117° C.), 2,3-dimethyl-1-butanol (142° C.), 3,3-dimethy-1-butanol (143° C.), 2-diethyl-1-butanol (146° C.), 2-methyl-1-butanol (129° C.), 3-methyl-1-butanol (131° C.), 2-butanol (99.5° C.), 2-methyl-2-butanol (102° C.), 2,3-dimethyl-2-butanol (118° C.), 3,3-dimethyl-2-butanol (120° C.), 3-methyl-2-butanol (112° C.), 2-methyl-1-pentanol (148° C.), 3-methyl-1-pentanol (152° C.), 4-methyl-1-pentanol (152° C.), 2-pentanol (119° C.), 2,4-dimethyl-2-pentanol (133° C.), 2-methyl-2-pentanol (120° C.), 3-methyl-2-pentanol (134° C.), 4-methyl-2-pentanol (133° C.), 3-pentanol (116° C.), 2,4,4-trimethyl-2-pentanol (147° C.), 2,2-dimethyl-3-pentanol (135° C.), 2,3-dimethyl-3-pentanol (140° C.), 2,4-dimethyl-3-pentanol (139° C.), 3-ethyl-3-pentanol (143° C.), 3-ethyl-2-methyl-3-pentanol (159° C.), 2-methyl-3-pentanol (127° C.), 2,3,4-trimethyl-3-pentanol (157° C.), 1-pentanol (138° C.) and 1-hexanol (158° C.), 2-hexanol (138° C.), 2-methyl-2-hexanol (143° C.), 5-methyl-2-hexanol (150° C. ), 3-hexanol (135° C.), and 3-methyl-3-hexanol (143° C.).

Volatile esters, such as methyl- and ethyl-esters of formic acid, acetic acid, propionic acid, butyric acid may also be useful as dispersing media. Exemplary dispersing media involving formic acid derivatives include, but are not limited to, allyl formate (83.6° C.), butyl formate (106.8° C.), isobutyl formate (98.4° C.), sec-butyl formate (97° C.), ethyl formate (54.5° C.), hexyl formate (156° C.), methyl formate (31.5° C.), pentyl formate (132° C.), isopentyl formate (124° C.), propyl formate (81.3° C.), and isopropyl formate (68° C.).

Exemplary dispersing media involving acetic acid derivatives include, but are not limited to, allyl acetate (103° C.), butyl acetate (126° C.), iso-butyl acetate (117° C.), sec-butyl acetate (112° C.), tert-butyl acetate (97° C.), ethyl acetate (77° C.), methyl acetate (57° C.), tert-amyl acetate (124° C.), isopentyl acetate (142° C.), 2-methyl-3-pentyl acetate (148° C.), 3-methyl-3-pentyl acetate (148° C.), 4-methyl-2-pentyl acetate (147° C.), pentyl acetate (139° C.), 2-pentyl acetate (130° C.), 3-pentyl acetate (132° C.), propyl acetate (101° C.), isopropyl acetate (90° C.), and 1,2,2-trimethyl propyl acetate (141° C.).

Exemplary dispersing media involving propionic acid derivatives include, but are not limited to, allyl propionate (124° C.), butyl propionate (145° C.), isobutyl propionate (136° C.), sec-butyl propionate (132° C.), ethyl propionate (99° C.), propyl propionate (122° C.), isopropyl propionate (109° C.), and methyl propionate (79.9° C.).

Exemplary dispersing media involving butyric acid derivatives include, but are not limited to, sec-butyl butyrate (151° C.), iso-butyl butyrate (157° C.), tert-butyl butyrate (145° C.), ethylbutyrate (121° C.), ethyl-2-methyl butyrate (131° C.), isopropyl-3-methyl butyrate(142° C.), ethyl isovalerate (134° C.), methyl isovalerate (116° C.), propyl isovalerate (156° C.), propyl butyrate (143° C.), and isopropyl butyrate (130° C.).

Exemplary ethers that can be used as dispersing media in accordance with the present invention include, but are not limited to, dimethyl ether (25° C.), diethyl ether (35° C.), dimethoxy ethane (85° C.), diethoxymethane (87° C.), dibutylether (142° C.), and isopropyl ether (68° C.).

Exemplary ketones and aldehydes useful as dispersing media in the present invention include, but are not limited to, acetaldehyde (21° C.), propionaldehyde (49° C.), butyraldehyde (75° C.), hexanal (131° C.), heptanal (153° C.), acetone (55° C.), butanone (80° C.), penantones (101–102° C.), hexanones (123–127° C.), and heptanones (145–150° C.).

The catalysts of the present invention may optionally be prepared using activators, which as those disclosed in Knopf et al., U.S. Pat. Nos. 4,754,075 and 4,886,917, as well as King, U.S. Pat. Nos. 5,114,900 and 5,120,697, all of which are incorporated by reference. In addition, aluminum alkoxide as disclosed in Leach et al. U.S. Pat. No. 4,835,321, which is incorporated by reference, may also be used to prepare the catalysts of the present invention.

In forming the catalyst according to the process of the present invention, water may be volatilized in the process. Alternatively, the dispersing media, the calcium-containing compound, the carboxylic acid, and the neutralizing acid can be reacted or combined under conditions that prevent any loss of water that is either initially present or formed during the reaction, thus forming a highly active catalyst. It is postulated that by keeping the water in the system during the reaction to form the catalyst, there is enhanced solubilization of the active calcium catalyst species that leads to the production of a more active catalyst. For example, if the reaction is conducted at elevated temperatures, super-atmospheric pressure can be used to prevent loss of water. Preferably, the reaction is conducted at elevated temperatures under total reflux to prevent loss of water.

B. Use of Catalyst

The catalyst prepared according to the process of the present invention can be used to alkoxylate compounds having active or labile hydrogen atoms, esters, and mixtures thereof. The substrates or reactants of the present invention include alcohols, phenols, polyols, carboxylic acids, amides, amines, esters and glycerides.

It will be appreciated that in some instances, the substrate and the dispersing media are the same. For example, it may be desirable to produce a butanol ethoxylate. The calcium catalyst can be prepared using butanol as the dispersing medium. To produce a butanol ethoxylate, the dispersing media is not removed prior to the alkoxylation process, and the butanol itself serves as the reactant or substrate for ethoxylation. In most other instances, the presence of the dispersing medium during the reaction results in unwanted by-products. Thus, when the substrate is different than the dispersing medium, the volatile dispersing media is removed prior to the alkoxylation process. The substrate has a boiling point greater than that of the dispersing medium. Preferably, the boiling point of the substrate is about 20° C. or more higher than the boiling point of the dispersing medium.

Suitable active hydrogen-containing compound starting materials (reactants) that can be employed in the alkoxylation process of the present invention include any permissible substituted or unsubstituted active hydrogen-containing organic compound(s). Non-limiting illustrative examples of active hydrogen-containing compounds useful in this invention include, for example, substituted and unsubstituted alcohols, phenols, carboxylic acids, amines, and the like. Preferred active hydrogen-containing compounds include alcohols and phenols, as, for example, substituted and unsubstituted alcohols (mono-, di-, and polyhydric alcohols), phenols, carboxylic acids (mono-, di-, and polyacids), and amines (primary and secondary). Other suitable active hydrogen-containing compounds include substituted and unsubstituted thiophenols, mercaptans, amides, and the like. Such organic compounds frequently contain 1 to about 50 carbons and can contain aliphatic and/or aromatic structures. Most often, the organic compounds are selected from the groups of mono-, di-, and trihydric alcohols having from 1 to about 30 carbon atoms.

Particularly preferred alcohols are primary and secondary monohydric alcohols which are straight or branched chain such as methanol, ethanol, propanol, butanol, pentanol, hexanol, heptanol, octanol, nonanol, decanol, undecanol, dodecanol, tridecanol, tetradecanol, pentadecanol, hexadecanol, octadecanol, isopropyl alcohol, sec-butanol, isobutanol, 2-pentanol, 3-pentanol, 2-ethylhexanol, isodecanol, and the like. Particularly suitable alcohols are linear and branched primary alcohols (including mixtures) such as produced by the "OXO" reaction of C5 to C20 olefins. The alcohols may also be cycloaliphatic such as cyclopentanol, cyclohexanol, cycloheptanol, cyclooctanol, as well as aromatic substituted aliphatic alcohols such as benzyl alcohol, phenylethyl alcohol, and phenylpropyl alcohol. Other aliphatic structures include 2-butoxy ethanol and the like, as well as substituted acrylics.

Preferred phenols include alkylphenyls of up to 30 carbons such as p-methylphenol, p-ethylphenol, p-butylphenol, p-heptylphenol, p-octylphenol, p-nonylphenol, dinonylphenol, p-decylphenol, and p-dodecylphenol, as well as dialkylphenols, such as ditertbutylphenols. The aromatic moiety may contain other substituents such as halide atoms.

Preferred polyhydric alcohols (polyols) having 2 or more hydroxyl groups, e.g., about two to six hydroxyl groups and have 2 to 30 carbons, include glycols such as ethylene glycol, propylene glycol, butylene glycol, pentylene glycol, hexylene glycol, neopentylene glycol, decylene glycol, diethylene glycol, triethylene glycol and dipropylene glycol. Other polyols include glycerin, 1,3-propanediol, pentaerythritol, galactitol, sorbitol, mannitol, erythritol, trimethylolethane and trimethylolpropane.

Preferred carboxylic acids include formic acid, acetic acid, propionic acid, butyric acid, valeric acid, caproic acid, caprylic acid, capric acid, lauric acid, myristic acid, palmitic acid, stearic acid, oleic acid, linoleic acid, etc. Other suitable carboxylic acids include benzoic acid, phenylacetic acid, toluic acid, and phthalic acid.

Preferred mono- amines and dialkyl and polyamines include N,N-diethylamine, N-diethylamine, N-butylamine, N-octylamine, N-decylamine, N-dodecylamine, diethanolamine, hexamethylenediamine, ethylenediamine, diethylenetriamine, and triethylenetetraamine.

Especially preferred active hydrogen-containing compounds include any permissible active hydrogen-containing organic compound such as those embraced by the formula:

$R_1(OH)_x$, wherein $R_1$ is the residue of an organic compound as defined above with respect to R and x is a value that satisfies the valencies of R, x preferably being a value of from about 1 to about 10, more preferably a value of from about 1 to about 4.

Esters that can be alkoxylated according to the process of the present invention include monoesters having the formula: R—CO—O—R; alkylene glycol diesters having the formula: R'—CO—O—$(CH_2)_n$—O—CO—R"; and triesters having the formula: R'—CO—O—$CH_2$—CH(OCOOR')—$CH_2$—O—CO—R', wherein R' and R", which can be the same or different, are each organic radicals containing from about 6 to about 30 carbon atoms; i.e., they can have generally the same connotation as given above for R, and n is from 2 to 12. Suitable esters and alkoxylated derivatives thereof are also disclosed in Weerasooriya et al., U.S. Pat. No. 5,386,045, and Leach et al., U.S. Pat. No. 5,220,046, which are incorporated herein by reference.

Other suitable substrates for the alkylation process include organic carbonates, such as those disclosed by Weerasooriya et al., U.S. Pat. No. 6,147,246, which is incorporated by reference.

In alkoxylating the active or labile hydrogen-containing or ester-containing compounds of the present invention, the alkylene oxides which provide the oxyalkylene units in the ethoxylated products include alkylene oxides such as ethylene oxide, propylene oxide, trimethylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorhydrin and epibromhydrin. The preferred alkylene oxides are ethylene oxide and propylene oxide. It will be understood that mixtures of such alkylene oxides, for example, mixtures of ethylene oxide and propylene oxide can be employed. Thus, it will be appreciated that the alkoxylated ester can contain an oxyalkylene chain which is heteric in nature (when a single alkylene oxide is used), block in nature (when two or more alkylene oxides are employed) or random in nature (when two or more alkylene oxides are employed).

In general, the amount of alkylene oxide used will be such as to provide an alkylene oxide content of from about 5 to about 95 percent by weight of the alkoxylated compound, and more preferably between about 10 to about 70 percent. It will be appreciated that the amount of the alkylene oxide employed can be varied over wide limits to tailor the end products for desired purposes. For example, in certain applications it is more desirable that the average number of alkoxy groups per substrate molecule be a relatively low number, e.g., from about 2 to about 4, whereas in other applications it is desirable that the number of alkoxy groups be greater, e.g., from about 6 to about 30.

In carrying out the alkoxylation reaction of the present invention, a substrate such as alcohol, ester, or the like is reacted with an alkylene oxide(s) in the presence of an alkoxylation catalyst prepared as per the process of the present invention. In general, the amount of catalyst employed will be from about 0.1 to about 20% by weight and more preferably about 0.1 to about 5% by weight based upon the total reaction mixture. For example, if the weight of the reaction mixture, including all alkylene oxide, is 300 g, typically from about 0.3 g to about 15 g of the alkoxylation catalyst will be employed in the reaction.

After removing the volatile organic dispersing medium, the alkoxylation process of the present invention can be conducted over a wide range of temperatures and pressure conditions. For example, the reaction can be conducted at temperature above about 120° C., preferably greater than about 150° C., even more preferably greater than about 160° C., and most preferably greater than about 170° C. The temperature is preferably no greater than about 190° C. to prevent self-polymorization where ethylene oxide is the alkoxylating agent. Generally, the temperature ranges between about 120° C. and 175° C., and preferably about 125° C. for propoxylation and 175° C. for ethoxylation. Pressures can range from ambient to about 100 psi with pressures from about 10 to about 60 psi being preferred.

Typically, the alkoxylation reaction of the present invention can be conducted by charging a suitable reaction vessel with the reactant, e.g., alcohol, ester, etc., in the desired amount. Typically, the reactant is heated to the desired elevated temperature under nitrogen or some other suitable inert gas, following which the reactor is placed under vacuum and/or nitrogen sparge to remove water. The alkoxylation catalyst produced as per the present invention is then injected into the reaction mixture and the purging temperature raised to the desired level under vacuum and/or nitrogen sparge to remove the volatiles. When the desired reaction temperature is reached, a slight nitrogen pressure is introduced and the chosen alkylene oxide, e.g., ethylene oxide, is introduced at the appropriate pressure. As the alkylene oxide reacts, additional amounts are added, the temperature being maintained substantially constant at the desired level throughout the reaction.

The catalytic alkoxylation reactions of this invention can be effected, for example, by conventional methods such as a batch processes. In a batch reactor, the catalyst is kept suspended in the reactant by recirculating and/or stirring.

To further illustrate the invention, the following non-limiting examples are presented.

EXAMPLE 1

Preparation of Alkoxylation Catalyst

In this example, an alkoxylation catalyst in accordance with the present invention and having the composition set forth in Table 1 was prepared in a batch process. To prepare the catalyst, a three-neck round bottom flask is equipped with a magnetic stir bar, a glass stopper, a Dean-Stark trap filled with n-butanol, a condenser topped with a calcium chloride drying tube, and is placed in an oil bath. The n-butanol is charged to the flask and stirring is initiated. The calcium hydroxide is slowly added, and allowed to stir for 15 minutes. A carboxylic acid (such as 2-ethylhexanoic acid) is then added to the mixture via syringe. The flask containing the mixture is then heated to above 120° C. at atmospheric pressure. The stirring suspension is allowed to reflux for up to about 8 hours. Under these conditions, water and the dispersing medium will be removed during the process, but the dispersing medium is recycled into the reaction vessel. After cooling to room temperature, the stir bar is removed, and an overhead stirrer is added. The Dean-Stark trap, condenser, drying tube, oil bath, and stoppers are removed. A source of nitrogen, thermometer, water bath, and presser equalizing dropping funnel are added. The pressure equalizing dropping funnel is charged with an inorganic acid (such as sulfuric acid), and the acid is added over the course of about 3 hours. The internal temperature is maintained at or below about 25° C. by use of the water bath and ice. After the acid is added completely, the suspension is allowed to stir for an additional 30–60 minutes at a temperature of about 25° C. Optionally, the heating and/or the water removal steps can be omitted partially or completely.

TABLE 1

Composition of Catalyst Formulation

| Component | % by mass |
|---|---|
| n-butanol | 72.8 |
| calcium hydroxide | 15.1 |
| 2-ethylhexanoic acid | 3.5 |
| sulfuric acid | 7.7 |

EXAMPLE 2

Preparation of Narrow Range Ethoxylate

The alkoxylation catalyst from Example 1 was used in this example to produce narrow range ethoxylates. More specifically, about 915 g of ALFOL® 1216CO alcohol (average molecular weight 196.2 g/mol) (Sasol North America, Inc.) was charged into a 2 gallon stainless steel autoclave equipped with an overhead stirrer, internal steam heating, water cooling, and thermocouple. The ALFOL® alcohol was first vacuum dried at about 200° F. (about 93° C.) for about ten minutes to remove residual moisture. Next, about 2.1 g of catalyst from Example 1 was added and vacuum (about 55 mm Hg) stripped at about 200° F. (about 93° C.) for about five minutes. In so doing, the volatile dispersing medium was removed from the catalyst.

The reactor was heated to about 282° F. (about 139° C.). A nitrogen blanket was introduced to maintain the proper nitrogen to ethylene oxide ratio. At an initial nitrogen pressure of about 10 psig, about 512.5 g of ethylene oxide (molecular weight 44.06 g/mol) was added at about 282 to 350° F. (about 139° C. to 177° C.). After the reaction, the product in the reactor was vacuum stripped at about 200° F. (about 93° C.) for about 15 minutes. The reaction yielded 1410 g of the 2.5 mole ethoxylate in 99% yield ("A1216CO-2.5EO NRE ethyloxylate"). The product did not require neutralization with an inorganic acid as the color stability was good with the pH in the neutral region.

Using similar techniques, 6.0, 9.5, and 30 mole ethoxylates of A1216CO were prepared. Likewise, 2.5, 6.0, 9.5, and 30 mole ethoxylates of isodecyl alcohol were prepared. In addition, 2.5, 6.0, 9.5, and 30 mole ethoxylates of nonylphenol were prepared. In an analogous manner, a 7.3 mole ethoxylate of methyl laurate was also prepared.

COMPARATIVE EXAMPLE 3

Broad Range Ethoxylate

A prior art broad range catalyst was prepared as a comparative example. A 25% solution of potassium hydroxide in methanol was prepared by dissolving granular KOH in methanol. Next 920 g of ALFOL® 1216CO alcohol and 2.4 g of KOH catalyst were reacted with 515.3 g of ethylene oxide. The product was neutralized with 0.8 g of acetic acid in order to maintain good color stability.

Using similar techniques, 6.0, 9.5, and 30 mole ethoxylates of A1216CO were prepared. Likewise, 2.5, 6.0, 9.5, and 30 mole ethoxylates of isodecyl alcohol were prepared. In addition, 2.5, 6.0, 9.5, and 30 mole ethoxylates of nonylphenol were prepared. Ethoyxylation of methyl laurate does not produce satisfactory results. See Weerasooriya, Ester Alkoxylation Technology, *Journal of Surfactants & Detergents*, Vol. 2 No. 3, pp 373–381 (1999).

EXAMPLE 4

Free Alcohol Comparison

In this example, the amount of free alcohol in the ethoxylated product was measured using C13 NMR. The results, which are shown in Tables 2 and 3, indicate that the NRE produced in accordance with the present invention contained significantly less free alcohol than the BRE.

TABLE 2

Free Alcohol Comparison for A1216CO Ethoxylates (measured by C13 NMR)

| Alcohol Ethoxylate | Mol % NRE | Mol % BRE |
|---|---|---|
| A1216CO-2.5EO | 20.4 | 32.0 |
| A1216CO-6.0EO | 2.6 | 5.3 |
| A1216CO-9.5EO | ND | 1.5 |
| A1216CO-30EO | ND | ND |

TABLE 3

Free Alcohol Comparison for Isodecyl Ethoxylates (measured by C13 NMR)

| Alcohol Ethoxylate | Mol % NRE | Mol % BRE |
|---|---|---|
| Isodecyl-2.5EO | 29.5 | 32.2 |
| Isodecyl-6.0EO | 11.4 | 22.1 |
| Isodecyl-9.5EO | 6.5 | 11.1 |
| Isodecyl-30EO | ND | ND |

EXAMPLE 5

Cloud Point Comparison

This example measured the cloud points of the alcohol ethoxylates produced in accordance with the present invention compared to the BRE catalysts of the prior art. The cloud point is the temperature at which a 1% non-ionic surfactant becomes insoluble in water as the sample is warmed. That is, cloud points are typically measured using 1% aqueous surfactant solutions. Cloud points range from 0° to 100° C. (32 to 212° F.), limited by the freezing and boiling points of water. Cloud points are characteristic of nonionic surfactants in that ethoxylates become less soluble in water at higher temperatures. In contrast, anionic surfactants (with negatively charged head groups) become more water-soluble as the temperature is raised. The cloud point therefore indicates the temperature at which the nonionic surfactant separates out of solution.

The results are shown in the table below:

TABLE 4

| Alcohol Ethoxylate | Cloud Point (° C.) (Free alcohol - mole %) | |
| --- | --- | --- |
|  | NRE | BRE |
| A1216CO-6.0EO | 42 (2.6) | 37 (5.3) |
| A1216CO-9.5EO | 87 (ND) | 86 (1.5) |
| Isodecyl-6EO | 43 (11.4) | 36 (22.1) |
| Isodecyl-9.5EO | 88 (6.5) | 84 (11.1) |
| Nonylphenol-9.5EO | 62 | 61 |

It is expected that by virtue of the catalyst system involved, the process disclosed in the Lin '121 Patent, King '900 Patent, and Leach '321 Patent will produce ethoxylates whose properties will be quite similar to those of the NREs of the present invention. However, the ethoxylates produced in accordance with the present invention will contain fewer by-products than those produced in accordance with the Lin '121 Patent.

From the foregoing it will be seen that this invention is one well adapted to attain all ends and objectives hereinabove set forth, together with the other advantages which are obvious and which are inherent to the invention. Further, since many possible embodiments may be made of the invention without departing from the scope thereof, it is to be understood that all matters herein set forth are to be interpreted as illustrative, and not in a limiting sense. Various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A process for preparing an alkoxylation catalyst comprising:
admixing a volatile dispersing medium consisting essentially of media having a boiling point less than 160° C. and consisting essentially of one or more
branched or straight chain alcohols,
volatile esters,
volatile ethers selected from the group consisting of dimethyl ether, diethyl ether, dimethoxy ethane, diethoxymethane, dibutylether, and isopropyl ether, or
volatile aldehydes and ketones,
and a calcium-containing compound that is at least partially dispersible in said dispersing medium and a carboxylic acid or anhydride having from about 4 to about 15 carbon atoms, with the mole ratio of calcium to said carboxylic acid or anhydride being from about 15:1 to 1:1, to produce a calcium-containing composition.

2. The process according to claim 1 further comprising the step of adding an amount of an inorganic acid or anhydride to produce a partially neutralized calcium-containing catalyst.

3. The process of claim 2 wherein said inorganic acid or anhydride is selected from the group consisting of sulfuric acid, phosphoric acid, oleum, sulfur trioxide, and phosphorous pentoxide, or mixtures thereof.

4. The process according to claim 2 further comprising the step of adding an aluminum alkoxide to the calcium-containing composition.

5. The process of claim 2 including heating said partially neutralized composition at a temperature of from about 25° C. to about 160° C. under reflux conditions.

6. The process of claim 5 wherein said heating is conducted for a period of 1 to 5 hours.

7. The process of claim 1 wherein said calcium-containing compound is selected from the group consisting of calcium hydride, calcium acetate, calcium oxalate, calcium oxide, calcium hydroxide, calcium lactate, calcium alkoxide, and mixtures thereof.

8. The process of claim 1 wherein said carboxylic acid is selected from the group consisting of octanoic acid, 2-methyl hexanoic acid, heptanoic acid, 3-methyl octanoic acid, 4-ethyl nonanoic acid, 2-ethyl hexanoic acid, or mixtures thereof.

9. The process of claim 1 wherein said dispersing medium consists essentially of one or more branched or straight chain alcohols.

10. The process of claim 9 wherein said branched or straight chain alcohols are selected from the group consisting of methanol, ethanol, 1-propanol, 2-propanol, 2-methyl-2-propanol, 1-butanol, 2,3-dimethyl-1-butanol, 3,3-dimethyl-1-butanol, 2-diethyl-1-butanol, 2-methyl-1-butanol, 3-methyl-1-butanol, 2-butanol, 2-methyl-2-butanol, 2,3-dimethyl-2-butanol, 3,3-dimethyl-2-butanol, 3-methyl-2-butanol, 2-methyl-1-pentanol, 3-methyl-1-pentanol, 4-methyl-1-pentanol, 2-pentanol, 2,4-dimethyl-2-pentanol, 2-methyl-2-pentanol, 3-methyl-2-pentanol, 4-methyl-2-pentanol, 3-pentanol, 2,4,4-trimethyl-2-pentanol, 2,2-dimethyl-3-pentanol, 2,3-dimethyl-3-pentanol, 2,4-dimethyl-3-pentanol, 3-ethyl-3-pentanol, 3-ethyl-2-methyl-3-pentanol, 2-methyl-3-pentanol, 2,3,4-trimethyl-3-pentanol, 1-pentanol, 1-hexanol, 2-hexanol, 2-methyl-2-hexanol, 5-methyl-2-hexanol, 3-hexanol, and 3-methyl-3-hexanol.

11. The process of claim 1 wherein said dispersing medium consists essentially of one or more volatile esters.

12. The process according to claim 11 wherein said ester is an ester of formic acid, acetic acid, propionic acid, or butyric acid.

13. The process according to claim 11 wherein said ester is selected from the group consisting of allyl formate, butyl formate, isobutyl formate, sec-butyl formate, ethyl formate, hexyl formate, methyl formate, pentyl formate, isopentyl formate, propyl formate, and isopropyl formate.

14. The process according to claim 11 wherein said ester is selected from the group consisting of allyl acetate, butyl acetate, iso-butyl acetate, sec-butyl acetate, tert-butyl acetate, ethyl acetate, methyl acetate, tert-amyl acetate, isopentyl acetate, 2-methyl-3-pentyl acetate, 3-methyl-3-pentyl acetate, 4-methyl-2-pentyl acetate, pentyl acetate, 2-pentyl acetate, 3-pentyl acetate, propyl acetate, isopropyl acetate, and 1,2,2-trimethyl propyl acetate.

15. The process according to claim 11 wherein said ester is selected from the group consisting of allyl propionate, butyl propionate, isobutyl propionate, sec-butyl propionate, ethyl propionate, propyl propionate, isopropyl propionate, and methyl propionate.

16. The process according to claim 11 wherein said ester is selected from the group consisting of sec-butyl butyrate, iso-butyl butyrate, tert-butyl butyrate, ethylbutyrate, ethyl-2-methyl butyrate, isopropyl-3-methyl butyrate, ethyl isovalerate, methyl isovalerate, propyl isovalerate, propyl butyrate, and iso-propyl butyrate.

17. The process of claim 1 wherein said dispersing medium consists essentially of one or more volatile ethers.

18. The process of claim 17 wherein said ether is selected from the group consisting of dimethyl ether, diethyl ether, dimethoxy ethane, diethoxymethane, dibutylether, and isopropyl ether.

19. The process of claim 1 wherein said dispersing medium consists essentially of one or more volatile aldehydes and ketones.

20. The process of claim 19 wherein said aldehydes and ketones are selected from the group consisting of acetaldehyde, propionaldehyde, butyraldehyde, hexanal, heptanal, acetone, butanone, pentanones, hexanones, and heptanones.

21. The process of claim 1 wherein said dispersing medium consists essentially of media having a boiling point less than 120° C.

22. The process of claim 1 wherein said dispersing medium consists essentially of media having a boiling point between about 80° C. and 140° C.

23. The process of claim 3 further comprising the step of removing the volatile dispersing medium to generate an active catalyst in a solid form.

24. A process for preparing an alkoxylation catalyst comprising:
admixing a volatile dispersing medium consisting of media having a boiling point less than 160° C. and consisting of one or more
branched or straight chain alcohols,
volatile esters,
volatile ethers selected from the group consisting of dimethyl ether, diethyl ether, dimethoxy ethane, diethoxymethane, dibutylether, and isopropyl ether, or
volatile aldehydes and ketones,
and a calcium-containing compound that is at least partially dispersible in said dispersing medium and a carboxylic acid or anhydride having from about 4 to about 15 carbon atoms, the mole ratio of calcium to said carboxylic acid or anhydride being from about 15:1 to 1:1, to produce a calcium-containing composition.

25. An alkoxylation process comprising:
forming an alkoxylation catalyst by admixing a volatile dispersing medium having a boiling point below about 160° C. and consisting essentially of one or more
branched or straight chain alcohols,
volatile esters,
volatile ethers selected from the group consisting of dimethyl ether, diethyl ether, dimethoxy ethane, diethoxymethane, dibutylether, and isopropyl ether, or
volatile aldehydes and ketones,
and a calcium-containing compound that is at least partially dispersible in said volatile dispersing medium, and a carboxylic acid or anhydride having from about 4 to about 15 carbon atoms, with the mole ratio of calcium to said carboxylic acid or anhydride being from about 15:1 to 1:1, to produce a calcium-containing composition having titratable alkalinity; and
adding an amount of inorganic acid or anhydride to produce a partially neutralized calcium-containing alkoxylation catalyst; and
reacting, in the presence of said alkoxylation catalyst, a reactant selected from the group consisting of alcohols, phenols, esters, glycerides, carboxylic acids, amides, and amines and mixtures thereof and an alkylene oxide under alkoxylation conditions to produce an alkoxylated derivative of said reactant.

26. The process of claim 25 wherein said reaction occurs at a temperature greater than about 160° C.

27. The process of claim 25 wherein said reactant is selected from the group consisting of methanol, ethanol, propanol, butanol, pentanol, hexanol, heptanol, octanol, nonanol, decanol, undecanol, dodecanol, tridecanol, tetradecanol, pentadecanol, hexadecanol, octadecanol, isopropyl alcohol, sec-butanol, isobutanol, 2-pentanol, 3-pentanol, 2-ethylhexanol, isodecanol, cyclopentanol, cyclohexanol, cycloheptanol, cyclooctanol, benzyl alcohol, phenylethyl alcohol, and phenylpropyl alcohol, and 2-butoxy ethanol.

28. The process of claim 25 wherein said reactant is selected from the group consisting of as p-methylphenol, p-ethylphenol, p-butylphenol, p-heptylphenol, p-octylphenol, p-nonylphenol, dinonylphenol, p-decylphenol, and p-dodecylphenol.

29. The process of claim 25 wherein said reactant is selected from the group consisting of ethylene glycol, propylene glycol, butylene glycol, pentylene glycol, hexylene glycol, neopentylene glycol, decylene glycol, diethylene glycol, triethylene glycol, and dipropylene glycol.

30. The process of claim 25 wherein said reactant is selected from the group consisting of glycerin, 1,3-propanediol, pentaerythritol, galactitol, sorbitol, mannitol, erythritol, trimethylolethane and trimethylolpropane.

31. The process of claim 25 wherein said reactant is selected from the group consisting of formic acid, acetic acid, propionic acid, butyric acid, valeric acid, caproic acid, caprylic acid, capric acid, laurie acid, myristic acid, palmitic acid, stearic acid, oleic acid, linoleic acid, benzoic acid, phenylacetic acid, toluic acid, and phthalic acid.

32. The process of claim 25 wherein said reactant is selected from the group consisting of N,N-diethylamine, N-ethylamine, N-butylamine, N-octylamine, N-decylamine, N-dodecylamine, diethanolamine, hexamethylenediamine, ethylenediamine, diethylenetriamine, and trietheylenetetraamine.

33. The process of claim 25 wherein said volatile dispersing media is the same as said reactant.

34. The process of claim 25 wherein said volatile dispersing media is removed prior to said reacting step.

35. The process of claim 25 wherein said reactant has a boiling point greater than the boiling point of said dispersing medium.

36. The process of claim 25 wherein the reactant has boiling point about 20° C. or more higher than the boiling point of said dispersing medium.

37. The process of claim 25 wherein said calcium-containing compound is selected from the group consisting of calcium hydride, calcium acetate, calcium oxalate, calcium oxide, calcium hydroxide, calcium lactate, calcium alkoxide, and mixtures thereof.

38. The process of claim 25 wherein said carboxylic acid is selected from the group consisting of octanoic acid, 2-methyl hexanoic acid, heptanoic acid, 3-methyl octanoic acid, 4-ethyl nonanoic acid, 2-ethyl hexanoic acid, or mixtures thereof.

39. The process of claim 25 wherein said inorganic acid or anhydride is selected from the group consisting of sulfuric acid, phosphoric acid, oleum, sulfur trioxide, and phosphorous pentoxide, or mixtures there of.

40. The process of claim 25 wherein said dispersing medium consists essentially of one or more branched or straight chain alcohols.

41. The process of claim 40 wherein said branched or straight chain alcohols are selected from the group consisting of methanol, ethanol, 1-propanol, 2-propanol, 2-methyl- 2-propanol, 1-butanol, 2,3-dimethyl-1-butanol, 3,3-dimethyl-1-butanol, 2-diethyl-1-butanol, 2-methyl-1-butanol, 3-methyl-1-butanol, 2-butanol, 2-methyl-2-butanol, 2,3-dimethyl-2-butanol, 2,3-dimethyl-2-butanol, 3,3-dimethyl-2-butanol, 3-methyl-2-butanol, 2-methyl-1-pentanol, 3-methyl-1-pentanol, 4-methyl-1-pentanol, 2-pentanol, 2,4-dimethyl-2-pentanol, 2-methyl-2-pentanol, 3-methyl-2-pentanol, 4-methyl-2-pentanol, 3-pentanol, 2,4,4-trimethyl-2-pentanol, 2,2-dimethyl-3-pentanol, 2,3-dimethyl-3-pentanol, 2,4-dimethyl-3-pentanol, 3-ethyl-3-pentanol, 3-ethyl-2-methyl-3-pentanol 2-methyl-3-pentanol, 2,3,4-trimethyl-3-pentanol, 1-pentanol, 1-hexanol, 2-hexanol, 2-methyl-2-hexanol, 5-methyl-2-hexanol, 3-hexanol, and 3-methyl-3-hexanol.

42. The process of claim 25 wherein said dispersing medium consists essentially of one or more volatile esters.

43. The process according to claim 42 wherein said ester is an ester of formic acid, acetic acid, propionic acid, or butyric acid.

44. The process according to claim 43 wherein said ester is selected from the group consisting of allyl formate, butyl formate, isobutyl formate, sec-butyl formate, ethyl formate, hexyl formate, methyl formate, pentyl formate, isopentyl formate, propyl formate, and isopropyl formate.

45. The process according to claim 43 wherein said ester is selected from the group consisting of allyl acetate, butyl acetate, iso-butyl acetate, sec-butyl acetate, tert-butyl acetate, ethyl acetate, methyl acetate, tert-amyl acetate, isopentyl acetate, 2-methyl-3-pentyl acetate, 3-methyl-3-pentyl acetate, 4-methyl-2-pentyl acetate, pentyl acetate, 2-pentyl acetate, 3-pentyl acetate, propyl acetate, isopropyl acetate, and 1,2,2-trimethyl propyl acetate.

46. The process according to claim 43 wherein said ester is selected from the group consisting of allyl propionate, butyl propionate, isobutyl propionate, sec-butyl propionate, ethyl propionate, propyl propionate, isopropyl propionate, and methyl propionate.

47. The process according to claim 43 wherein said ester is selected from the group consisting of sec-butyl butyrate, iso-butyl butyrate, tert-butyl butyrate, ethylbutyrate, ethyl-2-methyl butyrate, isopropyl-3-methyl butyrate, ethyl isovalerate, methyl isovalerate, propyl isovalerate, propyl butyrate, and iso-propyl butyrate.

48. The process of claim 25 wherein said dispersing medium consists essentially of one or more volatile ethers.

49. The process of claim 48 wherein said ether is selected from the group consisting of dimethyl ether, diethyl ether, dimethoxy ethane, diethoxymethane, dibutylether, and isopropyl ether.

50. The process of claim 25 wherein said dispersing medium consists essentially of one or more volatile aldehydes and ketones.

51. The process of claim 50 wherein said aldehydes and ketones are selected from the group consisting of acetaldehyde, propionaldehyde, butyraldehyde, hexanal, heptanal, acetone, butanone, pentanones, hexanones, and heptanones.

52. The process of claim 25 wherein said dispersing medium consists essentially of media having a boiling point less than 120° C.

53. The process of claim 25 wherein said dispersing medium consists essentially of media having a boiling point between about 80° C. and 140° C.

* * * * *